(12) United States Patent
Graβ et al.

(10) Patent No.: US 9,145,379 B2
(45) Date of Patent: Sep. 29, 2015

(54) 2,5-FURAN DICARBOXYLATE DERIVATIVES, AND USE THEREOF AS PLASTICIZERS

(75) Inventors: Michael Graβ, Haltern am See (DE); Hinnerk Gordon Becker, Essen (DE)

(73) Assignee: Evonik Degussa GmbH, Essen (DE)

( * ) Notice: Subject to any disclaimer, the term of this patent is extended or adjusted under 35 U.S.C. 154(b) by 662 days.

(21) Appl. No.: 13/392,974

(22) PCT Filed: Aug. 17, 2010

(86) PCT No.: PCT/EP2010/061941
§ 371 (c)(1),
(2), (4) Date: Apr. 30, 2012

(87) PCT Pub. No.: WO2011/023590
PCT Pub. Date: Mar. 3, 2011

(65) Prior Publication Data
US 2012/0220507 A1    Aug. 30, 2012

(30) Foreign Application Priority Data

Aug. 28, 2009  (DE) .......................... 10 2009 028 975

(51) Int. Cl.
| C08K 5/1535 | (2006.01) |
| C08K 5/10 | (2006.01) |
| C08F 14/06 | (2006.01) |
| C07D 307/68 | (2006.01) |

(52) U.S. Cl.
CPC .............. *C07D 307/68* (2013.01); *C08F 14/06* (2013.01); *C08K 5/10* (2013.01); *C08K 5/1535* (2013.01); *C08K 2201/014* (2013.01)

(58) Field of Classification Search
None
See application file for complete search history.

(56) References Cited

U.S. PATENT DOCUMENTS

| 3,259,636 | A  | * | 7/1966 | Lew ............................. 549/485 |
| 6,355,711 | B1 | * | 3/2002 | Godwin et al. ............... 524/285 |
| 7,786,201 | B2 |   | 8/2010 | Grass et al. |
| 7,964,658 | B2 |   | 6/2011 | Grass |
| 8,022,244 | B2 |   | 9/2011 | Grass et al. |
| 8,258,325 | B2 |   | 9/2012 | Grass et al. |
| 2007/0060768 | A1 | * | 3/2007 | Grass et al. ................... 560/103 |
| 2007/0179229 | A1 | * | 8/2007 | Grass ............................ 524/287 |
| 2008/0188601 | A1 | * | 8/2008 | Grass et al. ................... 524/321 |
| 2008/0245996 | A1 | * | 10/2008 | Grass et al. .............. 252/182.12 |
| 2009/0301348 | A1 | * | 12/2009 | Grass et al. ................ 106/287.2 |
| 2010/0305255 | A1 |   | 12/2010 | Grass |
| 2012/0202725 | A1 | * | 8/2012 | Grass et al. ................... 508/308 |
| 2012/0220507 | A1 | * | 8/2012 | Grass et al. ................... 508/309 |
| 2014/0128623 | A1 | * | 5/2014 | Janka et al. ................... 549/485 |

OTHER PUBLICATIONS

U.S. Appl. No. 13/393,120, filed Feb. 28, 2012, Grass, et al.
U.S. Appl. No. 14/008,425, filed Sep. 27, 2013, Becker, et al.
U.S. Appl. No. 14/001,177, filed Aug. 23, 2013, Becker, et al.
U.S. Appl. No. 14/001,597, filed Oct. 8, 2013, Becker, et al.
U.S. Appl. No. 14/001,338, filed Sep. 5, 2013, Becker, et al.
Sanderson, R.D., et al., "Synthesis and Evaluation of Dialkyl Furan-2,5-Dicarboxylates as Plasticizers for PVC," Journal of Applied Polymer Science, vol. 53, No. 13, pp. 1785-1793, (Sep. 26, 1994).
Crespo, J.E., et al., "Substitution of Di(2-ethylhexyl) Phthalate by Di(isononyl) Cyclohexane-1,2-Dicarboxylate as a Plasticizer for Industrial Vinyl Plastisol Formulations," Journal of Applied Polymer Science, vol. 104, pp. 1215-1220, (2007).
International Search Report Issued Oct. 28, 2010 in PCT/EP10/61941 Filed Aug. 17, 2010.

* cited by examiner

*Primary Examiner* — Joseph D Anthony
(74) *Attorney, Agent, or Firm* — Oblon, McClelland, Maier & Neustadt, L.L.P.

(57) ABSTRACT

The invention relates to mixtures of isononyl furan-2,5-dicarboxylate of formula (I), methods for producing said mixtures of isononyl furan-2,5-dicarboxylate of formula (I), compositions containing mixtures of isononyl furan-2,5-dicarboxylate of formula (I), uses of the mixtures of isononyl furan-2,5-dicarboxylate of formula (I) as plasticizers, and uses of the aforementioned compositions containing isononyl furan-2,5-dicarboxylate of formula (I).

20 Claims, No Drawings

2,5-FURAN DICARBOXYLATE DERIVATIVES, AND USE THEREOF AS PLASTICIZERS

The present invention relates to a mixture of esters of 2,5-furandicarboxylic acid (FDCA) with isomeric C9 alcohols, more particularly mixtures of linear and branched nonanols. The present invention likewise relates to a process for preparing such esters and mixtures and to the use thereof as plasticizers for polymers such as polyvinyl chloride, for example.

Polyvinyl chloride (PVC) is among the most economically important polymers. It finds diverse applications both as unplasticized PVC and as plasticized PVC.

To produce a plasticized PVC, the PVC is admixed with plasticizers, for which in the great majority of cases esters of phthalic acid are used, more particularly di-2-ethylhexyl phthalate (DEHP), diisononyl phthalate (DINP) and diisodecyl phthalate (DIDP). As a result of statutory regulations which already exist, and possible future such regulations, concerning the restricted use of phthalates, there is a need to find new esters suitable as plasticizers for PVC and other polymers, where preferably the same alcohols as before can be employed. On account of the limited availability of fossil raw materials, such esters ought in particular to have good market opportunities in the future, with at least the acid component being based on naturally occurring resources such as sugars, fats or oils.

In the publication "Top Value Added Chemicals from Biomass" by T. Werpy and G. Petersen (U.S. Dept. Of Energy (DOE); August 2004), 2,5-furandicarboxylic acid (FDCA) is regarded as one of the most promising platform chemicals on the basis of sugar. On account of its structural similarity with terephthalic acid, recent years have seen the publication of numerous papers on the use of 2,5-furandicarboxylic acid or various derivatives, primarily in polymers. The principal application in the majority of cases has been the partial or complete substitution of terephthalic acid or its derivatives in polymers. A very extensive review of FDCA, its applications, and its synthesis possibilities is found in the Internet publication by Jaroslaw Lewkowski, ARKIVOC 2001 (i), pages 17-54, ISSN 1424-6376, with the title "Synthesis, Chemistry and Applications of 5-hydroxymethylfurfural and its derivatives". Common to the majority of these syntheses is an acid-catalyzed reaction of carbohydrates, especially glucose or fructose, preferably fructose, to give 5-hydroxymethylfurfural (5-HMF), which can be isolated from the reaction medium by processing operations such as a two-phase regime, for example. Corresponding results have been described, for example, by Roman-Leshkov et al. in Science 2006, 312, pages 1933-1937, and by Zhang in Angewandte Chemie 2008, 120, pages 9485-9488.

In a further step, 5-HMF can then be oxidized to FDCA, as cited by Christensen in ChemSusChem 2007, 1, pp. 75-78, for example.

Also described, furthermore, is the preparation of certain FDCA esters by a direct synthesis starting from mucic acid (Tagouchi in Chemistry Letter vol. 37, No. 1 (2008)) and the corresponding alcohols.

The use of esters of 2,5-furandicarboxylic acid as plasticizers for plastics, more particularly PVC, PVB, PLA, PHB or PAMA, has not often hitherto been described. The most extensive review in this context is found in the publication by R. D. Sanderson et al. in Journal of Appl. Pol. Sci. 1994, vol. 53, pp. 1785 to 1793. Explicitly described there are the corresponding esters based on n-butanol, n-hexanol, 2-octanol, and 2-ethylhexanol. The investigations into the interaction of the esters with PVC show that they could be used as plasticizers for PVC. These conclusions, however, were derived only from DMTA measurements. Performance investigations, which are important and more meaningful for the processor, were not carried out. Nor is any reference made there, for example, to the fact that the 2-ethylhexyl ester of FDCA tends to crystallize at relatively low temperatures, as may be demonstrated by means of DSC measurements (melting point maximum at 12° C. with onset at −2.7° C.). Accordingly, for many processors, this ester will be of only limited usefulness, since at low temperatures there is no longer an assurance of pumpability.

A further factor is the classification of 2-ethylhexanol as a hazardous substance, which imposes limits on its usefulness, especially in sectors with skin contact and/or food contact.

Starting out from the known state of the art, therefore, the object was that of providing esters based on 2,5-furandicarboxylic acid that can be used as plasticizers for plastics such as PVC, PVB, PLA, PHB or PAMA, for example, with which the aforementioned problem does not occur, or occurs only in a markedly attenuated form, and which have the technical potential to replace the current standard petrochemical plasticizers.

It has been found that mixtures of isomeric nonyl esters of 2,5-furandicarboxylic acid (formula I) can be used as plasticizers for plastics, more particularly PVC, PVB, PLA, PHB, and PAMA, where they exhibit advantageous properties relative to the FDCA esters known from the literature. Moreover, relative to the corresponding esters of phthalic acid, these esters likewise exhibit performance advantages.

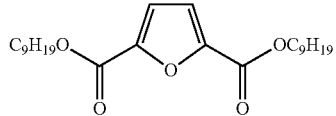

formula I

The present invention provides mixtures of isomeric nonyl esters of 2,5-furandicarboxylic acid of the formula I. Further provided by the present invention are compositions comprising the mixtures of isomeric nonyl esters of 2,5-furandicarboxylic acid of the formula I.

As far as the raw materials basis is concerned, the particular feature of the present invention lies in the optional utilization of renewable raw materials for preparing the furandicarboxylic esters of the invention. Renewable raw materials are understood in the sense of the present invention, in contradistinction to petrochemical raw materials, which are based on fossil resources, such as petroleum or coal, for example, to be those raw materials which form or are produced on the basis of biomass. The terms "biomass", "biobased" or "based on and/or produced from renewable raw materials" encompass all materials of biological origin, which come from what is called the "short-term carbon cycle", and hence are not part of geological formations or fossil strata. The identification and quantification of renewable raw materials is done in accordance with ASTM Method D6866. A characteristic of renewable raw materials among others is their fraction of the carbon isotope $^{14}C$, in contrast to petrochemical raw materials.

One particular economic and at the same time environmental advantage of the present invention lies in the simultaneous utilization of renewable and petrochemical raw materials for preparing the furandicarboxylic esters of the invention, this not only allowing particularly inexpensive production and broad applicability but also leading to particularly "sustainable" products.

The present invention further provides for the use of these mixtures in paints, inks or varnishes, in plastisols, adhesives or adhesives components, in sealants, as plasticizers in plastics or plastics components, as solvents, as a lubricating oil component and as an auxiliary in metals processing, and also provides a PVC composition or a plastisol comprising PVC and from 5 to 250 parts by mass of the mixture of the invention per 100 parts by mass of PVC.

The present invention also provides a process for preparing mixtures of isomeric nonyl esters of 2,5-furandicarboxylic acid, characterized in that 2,5-furandicarboxylic acid is esterified with a mixture of isomeric nononals, called isononanol below, optionally in the presence of a catalyst, or dimethyl 2,5-furandicarboxylate is transesterified with isononanol, with release of methanol, optionally using a catalyst, to give the mixture of isomeric nonyl esters of 2,5-furandicarboxylic acid.

For preparing a mixture of isomeric nonyl esters it is additionally possible to start from mucic acid as well, which, in the presence of isomeric nonanols and with preferably acidic catalysis, is simultaneously—in a one-pot reaction—cyclized and reacted to give the corresponding furandicarboxylic ester.

Relative to prior-art furandicarboxylic esters, but also relative to the present standard plasticizer di(isononyl) phthalate (DINP), the mixtures of isomeric nonyl esters of FDCA of the invention exhibit significantly improved properties in the context of their use as plasticizers in plastics, especially PVC.

Relative to the prior-art FDCA esters based on 2-ethylhexanol, the diisononyl esters of the invention have a lower volatility from the film and also, in plastisols, a lower increase in viscosity over time, and hence an enhanced aging stability. Furthermore, the isononanol-based ester mixture of the invention, in contrast to the di-2-ethylhexyl ester, shows no crystallization tendency in the range to −20° C., but instead has a glass transition point only about −80°. Interestingly, in terms of properties that are central to the user, the diisononyl esters of the invention also exhibit properties that are improved over those of the corresponding phthalate (diisononyl phthalate, DINP), such as, for example, more rapid gelling and improved plasticizing effect. For the processor, this means either a lower processing temperature or, for a given processing temperature, a higher production rate per unit time, combined with the effect that now less plasticizer is needed for the same degree of plasticity/flexibility than is the case with the corresponding phthalate.

The composition of the mixtures of isomeric nonyl esters of 2,5-furandicarboxylic acid, of the invention, is preferably such that the mixture comprises at least two different esters which differ in the constitution of the isomeric C9 radicals, with none of the C9 radicals present in the mixture having a fraction of more than 90 mol %.

The mixture of the invention may either consist exclusively of the mixtures of the esters of the formula I or as well as these may comprise at least one polymer and/or at least one plasticizer which is not a diester of the formula I. The plasticizers may be selected, for example, from trialkylesters of citric acid, acylated trialkylesters of citric acid, glycerol esters, glycol dibenzoates, alkyl benzoates, dialkyl adipates, trialkyl trimellitates, dialkyl terephthalates, dialkyl phthalates or the dialkyl esters of 1,2-, 1,3- or 1,4-cyclohexanedicarboxylic acids, the alkyl radicals having from 4 to 13, preferably 5, 6, 7, 8, 9, 10, 11 or 13, carbon atoms. The plasticizers may also be dianhydrohexitol esters, preferably isosorbide diesters of carboxylic acids, such as n- or isobutyric acid, valeric acid or 2-ethylhexanoic acid or isononanoic acid, for example.

Polymers which may be present in the mixture of the invention are, for example, polyvinyl chloride (PVC), polyvinyl butyral (PVB), polylactic acid (PLA), polyhydroxybutyral (PHB), and polyalkyl methacrylates (PAMA). With particular preference the polymer is polyvinyl chloride (PVC).

In preferred mixtures which comprise diesters of the formula I and polymers, the mass ratio of polymer/polymers to diester/diesters of the formula I is preferably from 30:1 to 1:2.5 and more preferably from 20:1 to 1:2.

In preferred mixtures comprising diesters of the formula I and plasticizers which are not a diester of the formula I, the molar ratio of plasticizers, more particularly of alkyl benzoates, dialkyl adipates, glycerol esters, trialkylesters of citric acid, acylated trialkylesters of citric acid, trialkyl trimellitates, glycol dibenzoates, dialkyl terephthalates, dialkyl phthalates, dialkanoyl esters of isosorbide and/or the dialkyl esters of 1,2-, 1,3- or 1,4-cyclohexanedicarboxylic acids, to diester/diesters of the formula I is preferably from 1:15 to 15:1, more preferably from 1:6 to 6:1.

The mixtures of diesters of the formula I of the invention, and the diesters of the formula I themselves, can be prepared in various ways. Preferably the mixtures of diesters of the formula I and/or the diesters of the formula I are prepared by the process described below.

The process of the invention for preparing isomeric nonyl esters of 2,5-furandicarboxylic acid is distinguished by the fact that 2,5-furandicarboxylic acid or a relatively short-chain dialkyl ester of this compound, especially the dimethyl ester, is reacted with a mixture of isomeric nonanols, with a catalyst being used optionally. Furthermore, the 2,5-furandicarbonyl dichloride which may be obtained by reacting the FDCA with chlorinating agents such as thionyl chloride, for example, can be used as a starting material for preparing diisononyl esters. Suitable conditions for the reaction of FDCA to give the diisononyl ester via the dichloride as intermediate are found in the examples.

It is preferred to use a mixture of isomeric nonanols which comprises at least two nonanols of empirical formula $C_8H_{17}CH_2OH$ with different constitutional formulae, with none of the nonyl alcohols present in the mixture having a fraction of preferably more than 90 mol %.

Preferably, the mixtures of isomeric nonanols of empirical formula $C_9H_{19}OH$, more particularly of formula $C_8H_{17}CH_2OH$, that are used in the process of the invention contain less than 10 mol %, preferably less than 5 mol %, more preferably less than 1 mol %, and more particularly from 0 to 0.5 mol %, preferably less than 0.1 mol %, more particularly from 0.0001 to 0.1 mol %, and with particular preference less than 0.05 mol %, more particularly from 0.01 to 0.05 mol %, of 3,5,5-trimethylhexanol or other trisubstituted nonyl alcohols having the empirical formula $C_8H_{17}CH_2OH$, especially those with quaternary C atoms. The presence of these alcohols impairs the performance properties and reduces the rate of biodegradation of the molecule.

It may be advantageous, furthermore, if the isononanols of empirical formula $C_9H_{19}OH$, more particularly of formula $C_8H_{17}CH_2OH$, that are used for preparing the diesters of the formula I present in the mixture of the invention contain 1% to 85%, more particularly 1% to 50%, preferably 2% to 20%, of n-nonanol.

The isomer distributions of the isomeric alcohols in the mixtures can be determined using the customary measurement methods familiar to the skilled person, such as NMR spectroscopy, GC or GC/MS spectroscopy, preferably following conversion into the silyl or methyl esters.

Synthesis of the Isomeric Nonyl Alcohols

In principle, all technical mixtures of nonanols having the empirical formula $C_9H_{19}OH$, more particularly those having the formula $C_8H_{17}CH_2OH$, that have at least two different constitutional isomers can be used. It is preferred to use those mixtures of isomeric nonanols with the formula $C_8H_{17}CH_2OH$ that in terms of the fraction of the different isomers and/or of the amount of C9 alcohols with quaternary C atoms are situated within the ranges indicated above.

The mixtures of isomeric nonanols with the empirical formula $C_9H_{19}OH$, more particularly the formula $C_8H_{17}CH_2OH$ (called isononanols below), that are used in the process of the invention may be prepared, for example, by hydroformylation of octenes, which in turn may be produced in a variety of ways, and subsequent hydrogenation.

As a raw material for preparing the octenes it is possible to use technical $C_4$ streams which initially contain all the isomeric $C_4$ olefins as well as the saturated butanes and possibly impurities such as $C_3$ and $C_5$ olefins and acetylenic compounds. Oligomerization of the olefins present in the $C_4$ streams produces predominantly isomeric octene mixtures along with higher oligomers such as $C_{12}$ and $C_{16}$ olefin mixtures. These octene mixtures, possibly after distillative removal of the $C_{12}$ and $C_{16}$ olefins, can be hydroformylated to the corresponding aldehydes and subsequently hydrogenated to the alcohol. The composition, i.e., the isomer distribution, of the technical nonanol mixtures is dependent on the starting material and substantially dependent on the oligomerization and hydroformylation processes.

The octene mixtures which can be used include, for example, those obtained by the process known as the Polygas process, in which $C_3/C_4$ mixtures are oligomerized over a solid acidic catalyst, preferably a solid phosphoric acid catalyst (SPA process). This process is described in documents including U.S. Pat. Nos. 6,284,938, 6,080,903, 6,072,093, 6,025,533, 5,990,367, 5,895,830, 5,856,604, 5,847,252, and 5,081,086. If olefin mixtures obtained exclusively in this way are hydroformylated, the product generally also includes fractions of octanals and decanals as well, and so here the average chain length may deviate from 9 carbon atoms. After the hydrogenation, therefore, a mixture is obtained which contains isomeric nonanols and which may also contain isomeric octanols or decanols as well. Furthermore, octenes from the oligomerization of ethylene can also be used with advantage.

Particularly preferred mixtures of isomeric nonanols that can be used in the process of the invention are those obtainable by hydroformylating isomeric octenes and subsequently hydrogenating the resultant aldehydes, with the mixture of isomeric octenes being obtained by contacting a hydrocarbon mixture comprising butenes, having an isobutene fraction of preferably less than 20% by mass, more preferably less than 10% by mass, very preferably less than 5% by mass, more preferably less than 3% by mass, with particular preference less than 1% by mass, preferably between 0.01% and 1% by mass, and more preferably between 0.05% and 0.5% by mass, based on the butenes, with an oligomerization catalyst, more particularly a catalyst containing nickel oxide. The preparation of isomeric octenes by oligomerization of substantially linear butenes over supported nickel catalysts is known, for example, in the form of an OCTOL process, which is described in EP 0 395 857 or EP 1 029 839, for example. In variants of the OCTOL process, catalysts containing Ti or Zr, for example, are used. Such alternative variants and particularly the catalysts are described in EP 1 171 413, for example. As already described above, the resultant octenes can be separated from the higher olefins—that is, from the $C_{12}$, $C_{16}$, $C_{20}$, etc. olefins—by means of distillation, for example.

The octenes or mixtures of isomeric octenes prepared as described above, for example, are subsequently passed on to a hydroformylation. The hydroformylation may take place in the presence of modified or nonmodified cobalt or rhodium catalysts. The hydroformylation takes place preferably in the presence of nonmodified cobalt compounds. Suitable hydroformylation processes are known from EP 0 850 905 and EP 1 172 349, for example. Generally speaking, a mixture is obtained in this way that is made up of substantially isomeric nonanals, optionally octenes that have not yet reacted, and also the corresponding mixtures of isomeric nonanols and octanes formed by hydrogenation (follow-on reaction).

The hydroformylation may also take place in the presence of rhodium catalysts. Hydroformylation processes of this kind are common knowledge, as for example from EP 0 213 639, EP 1 201 675, WO 03/16320, WO 03/16321, WO 2005/090276, and the documents cited therein. Specialty processes for the hydroformylation, which are likewise suitable for preparing mixtures of isomeric nonanols that can be used in the process of the invention, are described in WO 2004/020380 or DE 103 27 435, for example. The processes described therein are carried out in the presence of cyclic carbonic esters.

It may also be advantageous to fractionate the mixture of isomeric octenes to start with, as described in EP 1 172 349, before passing it on to the hydroformylation. In this way it is possible to obtain octene fractions which are especially suitable for the preparation of mixtures of isomeric nonanols that can be used in the process of the invention. From the fractions it is then possible in a relatively simple way, by mixing appropriate fractions, to obtain a mixture of isomeric octenes which is suitable for preparing mixtures of isomeric nonanols for use in the process of the invention.

The hydroformylation of the octene mixtures may be carried out in one or more stages, optionally with removal of the unreacted octenes after each stage. The reaction mixture obtained from the hydroformylation can optionally be—and preferably is—fractionated, thereby concentrating the nonanal fraction destined for the hydrogenation. Generally speaking, however, the hydroformylation product will be directly freed from the catalyst and thereafter fed to the hydrogenation. The hydrogenation takes place in general over heterogeneous catalysts at elevated temperatures and pressures in a conventional liquid-phase or gas-phase regime, as disclosed in WO 2009/027135, for example.

Suitable isononanol mixtures in the sense of the present invention are also specified in EP1171413, for example.

Furandicarboxylic Acid

Furan-2,5-dicarboxylic acid (FDCA, CAS No: 3238-40-2), a white solid having a melting point>300° C., has not hitherto been available on an industrial scale, but can either be prepared as per the literature or acquired commercially. The conversion into the dichloride, which may be desired or preferred, is described at length in the examples.

Esterification

For preparing the esters of the invention, either furandicarboxylic acid or a reactive derivative such as the corresponding dichloride, for example (see examples), is reacted with a mixture of isomeric nonanols. The esterification takes place preferably starting from furandicarboxylic acid and isononanol, with the aid of a catalyst.

The esterification of the furandicarboxylic acid with an isononanol mixture to give the corresponding esters may be carried out autocatalytically or catalytically, with Brönsted or Lewis acids, for example. Irrespective of the type of catalysis selected, there is always a temperature-dependent equilibrium developed between the reactants (acid and alcohol) and the products (ester and water). In order to shift the equilibrium in favor of the ester, an azeotrope former can be used to help remove the water of reaction from the batch. Since the alcohol mixtures used for the esterification boil at a lower temperature than the furandicarboxylic acid, its reactive derivatives, and its esters, and exhibit a miscibility gap with water, they are frequently used as azeotrope former, and can be recycled to the process following removal of water.

The alcohol used to form the ester, or the isomeric nonanol mixture which serves simultaneously as azeotrope former, is employed in excess, preferably 5% to 50% by mass, more particularly 10% to 30% by mass of the amount needed to form the ester.

As esterification catalysts it is possible to use acids, such as sulfuric acid, methanesulfonic acid or p-toluenesulfonic acid, for example, or metals or compounds thereof. Suitable examples include tin, titanium, and zirconium, which are used as finely divided metals or usefully in the form of their salts, oxides or soluble organic compounds. In contrast to protic acids, the metal catalysts are high-temperature catalysts which often attain their full activity only at temperatures upward of 180° C. Here, however, it should be borne in mind that the furandicarboxylic acid tends to give off $CO_2$ at temperatures above 190° C., and then the monocarboxylic acid is formed therefrom, and can no longer be reacted to give the target product. The metal catalysts, however, are preferably used, since in comparison to the proton catalysis they form fewer by-products from the alcohol used, such as olefins, for example. Exemplary representatives of metal catalysts are tin powder, tin(II) oxide, tin(II) oxalate, titanic esters such as tetraisopropyl orthotitanate or tetrabutyl orthotitanate, and zirconium esters such as tetrabutyl zirconate.

The catalyst concentration is dependent on the type of catalyst. In the case of the titanium compounds preferably employed, the concentration is 0.005% to 2.0% by mass, based on the reaction mixture, more particularly 0.01% to 0.5% by mass, especially 0.01% to 0.1% by mass.

The reaction temperatures when using titanium catalysts are between 160° C. and 270° C., preferably 160 to 200° C. The optimum temperatures are dependent on the reactants, reaction progress, and catalyst concentration. They may be easily determined by experiments for each individual case. Higher temperatures increase the reaction rates and promote secondary reactions, such as elimination of water from alcohols or formation of colored by-products, for example. A beneficial fact in relation to the removal of the water of reaction is that the alcohol can be distilled off from the reaction mixture. The desired temperature or desired temperature range can be brought about by the pressure in the reaction vessel. In the case of low-boiling alcohols, therefore, the reaction is carried out at superatmospheric pressure, and at reduced pressure in the case of higher-boiling alcohols. In the case of the reaction of FDCA with a mixture of isomeric nonanols, for example, operation takes place in a temperature range from 160° C. to 190° C. in the pressure range from 0.1 MPa to 0.001 MPa.

The quantity of liquid to be recycled to the reaction may consist wholly or partly of alcohol obtained by working up the azeotrope distillate. It is also possible to carry out the workup at a later point in time and to replace some or all of the liquid quantity removed with fresh alcohol, i.e., from an alcohol standing ready in a reservoir vessel.

The crude ester mixtures, which in addition to the ester or esters include alcohol, catalyst or its subsequent products, and optionally by-products, are worked up by conventional methods. This workup encompasses the following steps: removing excess alcohol and, when present, low boilers; neutralizing the acids present; optionally a steam distillation; converting the catalyst into a residue which is easily filterable; removing the solids; and, optionally, drying. The sequence of these steps may differ according to the workup procedure employed.

The mixture of the diisononyl esters may optionally be separated from the reaction mixture by distillation, optionally after neutralization of the batch.

Transesterification

The diisononyl esters of the invention can alternatively be obtained by transesterifying a furan-2,5-dicarboxylic diester with an isononanol mixture. Reactants used are furan-2,5-dicarboxylic diesters whose alkyl radicals attached to the O atom of the ester group have 1-8 C atoms. These radicals may be aliphatic, straight-chain or branched, alicyclic or aromatic. One or more methylene groups in these alkyl radicals may be substituted by oxygen. It is advantageous for the alcohols on which the reactant ester is based to boil at a temperature lower than the isononanol mixture used. One preferred reactant is dimethyl furan-2,5-dicarboxylate.

The transesterification is carried out catalytically, using Brönsted or Lewis acids or using bases, for example. Irrespective of which catalyst is used, there is always a temperature-dependent equilibrium developed between the reactants (dialkyl ester and isononanol mixture) and the products (diisononyl ester mixture and alcohol liberated). In order to shift the equilibrium in favor of the diisononyl ester mixture, the alcohol resulting from the reactant ester is removed from the reaction mixture by distillation.

Here as well it is useful to use the isononanol mixture in excess. As transesterification catalysts it is possible to use acids, such as sulfuric acid, methanesulfonic acid or p-toluenesulfonic acid, for example, or metals or compounds thereof. Suitable examples include tin, titanium, and zirconium, which are used as finely divided metals or usefully in the form of their salts, oxides or soluble organic compounds. In contrast to protic acids, the metal catalysts are high-temperature catalysts which attain their full activity only at temperatures upward of 180° C. They, however, are preferably used, since in comparison to the proton catalysis they form fewer by-products from the alcohol used, such as olefins, for example. Exemplary representatives of metal catalysts are tin powder, tin(II) oxide, tin(II) oxalate, titanic esters such as tetraisopropyl orthotitanate or tetrabutyl orthotitanate, and zirconium esters such as tetrabutyl zirconate.

In addition it is possible to use basic catalysts, such as oxides, hydroxides, hydrogencarbonates, carbonates or alkoxides of alkali metals or alkaline earth metals, for example. From this group it is preferred to use alkoxides, such as sodium methoxide, for example. Alkoxides may also be prepared in situ from an alkali metal and a nonanol and/or an isononanol mixture.

The catalyst concentration is dependent on the type of catalyst. It is typically between 0.005% to 2.0% by mass, based on the reaction mixture.

The reaction temperatures for the transesterification are typically between 100 and 220° C. They must at least be high enough to allow the alcohol formed from the reactant ester to be removed by distillation at the defined pressure, usually atmospheric pressure, from the reaction mixture.

The transesterification mixtures can be worked up in exactly the same way as described for the esterification mixtures.

Use

The mixtures of isomeric nonyl esters of 2,5-furandicarboxylic acid of the invention can be used as plasticizers, especially in plastics compositions, adhesives, sealants, varnishes, paints, plastisols, synthetic leathers, floorcoverings, underbody protection, coated fabrics, wallpapers or inks. The plasticizers of the invention can be used with preference in profiles, gaskets, food packaging, films, toys, medical articles, roofing sheets, synthetic leathers, floorcoverings, underbody protection, coated fabrics, wallpapers, cables and wire sheathing, and with particular preference in food packaging, toys, medical articles, such as in bags and tube material for infusions, dialysis, and drains, for example, wallpapers, floorcoverings, and coated fabrics.

Obtainable using the mixtures of isomeric nonyl esters of 2,5-furandicarboxylic acid of the invention are, in particular, compositions of the invention which comprise the mixture of isomeric nonyl esters of 2,5-furandicarboxylic acid.

Compositions of this kind may comprise the mixture of isomeric nonyl esters of 2,5-furandicarboxylic acid of the invention alone or in mixtures with other plasticizers. Where the compositions of the invention comprise the mixture of isomeric nonyl esters of 2,5-furandicarboxylic acid of the invention in a mixture with other plasticizers, the other plasticizers may be selected preferably from the group of the dialkyl phthalates, preferably with 4 to 13 C atoms in the alkyl chain; trialkyl trimellitates, preferably with 4 to 10 C atoms in the side chain; dialkyl adipates and preferably dialkyl terephthalates each preferably with 4 to 13 C atoms in the side chain; 1,2-cyclohexanedicarboxylic alkyl esters, 1,3-cyclohexanedicarboxylic alkyl esters, and 1,4-cyclohexanedicarboxylic alkyl esters, preferably 1,2-cyclohexanedicarboxylic alkyl esters, each preferably with alkyl=alkyl radical having 4 to 13 carbon atoms in the side chain; dibenzoic esters of glycols; alkylsulfonic esters of phenol with preferably an alkyl radical containing 8 to 22 C atoms; polymer plasticizers, glycerol esters, isosorbide esters, and alkyl benzoates, preferably having 7 to 13 C atoms in the alkyl chain. In all cases the alkyl radicals may be linear or branched and also identical or different. With particular preference the composition, in addition to the mixture of isomeric nonyl esters of 2,5-furandicarboxylic acid, comprises, in particular, an alkyl benzoate with alkyl=alkyl radical having 7 to 13 carbon atoms, preferably isononyl benzoate, nonyl benzoate, isodecyl benzoate, propylhelptyl benzoate or decyl benzoate. The fraction of mixtures of isomeric nonyl esters of 2,5-furandicarboxylic acid of the invention in the mixture with other plasticizers is preferably 15% to 90% by mass, more preferably 20% to 80% by mass, and very preferably 30% to 70% by mass, with the mass fractions of all of the plasticizers present adding up to give 100% by mass.

The stated compositions comprising mixtures of isomeric nonyl esters of 2,5-furandicarboxylic acid and other plasticizers may be used as a plasticizer composition in plastics compositions, adhesives, sealants, varnishes, paints, plastisols or inks. Examples of plastics products produced from the plasticizer compositions of the invention may include the following: profiles, gaskets, food packaging, films, toys, medical articles, roofing sheets, synthetic leathers, floorcoverings, underbody protection, coated fabrics, wallpapers, cables and wire sheathing. Preferred from this group are food packaging, toys, medical articles, wallpapers, coated fabrics, and floorcoverings.

The compositions of the invention which comprise a mixture of isomeric nonyl esters of 2,5-furandicarboxylic acid may comprise a polymer selected from polyvinyl chloride (PVC), polyvinylidene chloride (PVDC), polyacrylates, more particularly polymethyl methacrylate (PMMA), polyalkyl methacrylate (PAMA), fluoropolymers, more particularly polyvinylidene fluoride (PVDF), polytetrafluoroethylene (PTFE), polyvinyl acetate (PVAc), polyvinyl alcohol (PVA), polyvinylacetals, more particularly polyvinylbutyral (PVB), polystyrene polymers, more particularly polystyrene (PS), expandable polystyrene (EPS), acrylonitrile-styrene-acrylate (ASA), styrene-acrylonitrile (SAN), acrylonitrile-butadiene-styrene (ABS), styrene-maleic anhydride copolymer (SMA), styrene-methacrylic acid copolymer, polyolefins, more particularly polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulfides (PSu), biopolymers, more particularly polylactic acid (PLA), polyhydroxybutyral (PHB), polyhydroxyvaleric acid (PHV), polyesters, starch, cellulose and cellulose derivatives, more particularly nitrocellulose (NC), ethylcellulose (EC), cellulose acetate (CA), cellulose acetate/butyrate (CAB), rubber or silicones, and also mixtures or copolymers of the stated polymers or their monomeric units. The compositions of the invention preferably comprise PVC or homopolymers or copolymers based on ethylene, propylene, butadiene, vinyl acetate, glycidyl acrylate, glycidyl methacrylate, methacrylates, acrylates, acrylates or methacrylates having alkyl radicals, attached on the oxygen atom of the ester group, from branched or unbranched alcohols having one to ten carbon atoms, styrene, acrylonitrile or cyclic olefins.

The type of PVC in the composition of the invention is preferably suspension PVC, bulk PVC, microsuspension PVC or emulsion PVC. Based on 100 parts by mass of polymer, the compositions of the invention comprise preferably from 5 to 200, more preferably from 10 to 150, parts by mass of plasticizer.

In addition to the stated constituents, the compositions of the invention may comprise further constituents, more particularly, for example, other plasticizers, fillers, pigments, stabilizers, co-stabilizers such as epoxidized soybean oil, for example, and also lubricants, flowing agents, kickers, antioxidants or biocides.

The compositions of the invention take the form preferably of a liquid, more particularly a pumpable liquid, a paste, protection compound, plastisol, powder, solid or solid body.

The stated compositions comprising said polymers may be used as adhesives, sealants, varnishes, paints, plastisols, synthetic leathers, floorcoverings, underbody protection, fabric coatings, wallpapers or inks or for producing same.

Where the stated compositions comprise plastics, they can be processed to profiles, gaskets, one-part or multi-part closure devices, food packaging, films, toys, medical articles, more particularly bags and tube material, as used for infusions, dialysis, and drains, for example, roofing sheets, synthetic leathers, floorcoverings, underbody protection, coated fabrics, wallpapers, cables, and wire sheathing. The compositions of the invention are used preferably for producing food packaging, toys, medical articles, wallpapers, and floorcoverings.

The examples which follow are intended to illustrate the invention without restricting its scope of application, which is evident from the description and the claims. Even without further remarks, it is assumed that the skilled person is able to utilize the present invention in the widest conceivable scope.

EXAMPLES

The esters of the invention were prepared in a two-stage synthesis starting from furan-2,5-dicarboxylic acid via the dichloride.

Example 1

Synthesis Procedure for Furan-2,5-dicarbonyl dichloride (II)

A 250 ml three-neck flask with reflux condenser and dropping funnel was charged under argon with 72.1 g (462 mmol) of furan-2,5-dicarboxylic acid. Over a period of 10 minutes, 165 g (1.39 mol) of thionyl chloride, to which a few drops of N,N-dimethylformamide were added, were added. The suspension was heated to reflux temperature and the resulting gas was taken off through wash bottles containing aqueous KOH solution. The suspension was then heated for 4 hours under reflux until the evolution of gas was at an end and the dissolution of the solid was complete.

Following removal of excess thionyl chloride, the product was isolated by distillative purification (T=110° C., p=0.0012 MPa).

This gave 79.4 g of dichloride as a colorless crystalline solid (yield 89%) having a melting point of 79.5-80.0° C.

Furan-2,5-dicarbonyl dichloride was stored under inert gas (argon) in the dark at room temperature before being used further.

Example 2

Synthesis of Furan-2,5-dicarboxylic esters

Under argon, a three-neck flask with reflux condenser and dropping funnel was charged with the dichloride, which was melted by heating. Added dropwise slowly to the liquid were 2.4 equivalents of alcohol, and an exothermic reaction took place with evolution of gas.

The gas produced was passed through wash bottles containing aqueous KOH solution. Following complete addition, the mixture was stirred at a temperature of 80-100° C. for 16 hours.

The excess alcohol was removed under reduced pressure in the presence of boiling chips, and the crude product was purified by distillation.

For the synthesis of the comparative example, commercially available 2-ethylhexanol was used. For preparing the ester mixture of the invention, isononanol from the applicant, CAS No. 27458-94-2, available commercially under the product name Isononanol INA, was used. The isononanol used has a density (to DIN 51757) at 20° C. of 0.8348 g/cm$^3$, a refractive index (to DIN 51423/2) at 20° C. of 1.4362, and a shear viscosity (to DIN 53015) at 20° C. of 13.2 mPa·s, and also a solidification point<−75° C., and had the following composition as determined by gas-chromatographic analysis: 7.5 mol % n-nonanol; 19.8 mol % 6-methyloctanol; 20.0 mol % 4-methyloctanol; 3.8 mol % 2-methyloctanol; 8.3 mol % 3-ethylheptanol; 2.1 mol % 2-ethylheptanol; 1.8 mol % 2-propylhexanol; 15.0 mol % 4,5-dimethylheptanol; 10.1 mol % 2,5-dimethylheptanol; 2.5 mol % 2,3-dimethylheptanol; 4.1 mol % 3-ethyl-4-methylhexanol; 2.9 mol % 2-ethyl-4-methylhexanol; 2.1 mol % other, unidentified compounds having 9 carbon atoms; the sum total of the specified components was 100 mol %.

Table 1 below records the results of the two syntheses.

TABLE 1

| Ester | Boiling point of ester | Yield |
| --- | --- | --- |
| Bis(2-ethylhexyl) furan-2,5-dicarboxylate II (comparative example) | 137-138° C. (p = 0.0002 · MPa) | 99% |
| Bis(isononyl) furan-2,5-dicarboxylate (I) (inventive) | 155-185° C. (p = 0.0004 · MPa) | 98% |

The conversions of furan-2,5-dicarbonyl dichloride (2) to the corresponding esters are therefore virtually quantitative.

Example 3

Determination of the Low-Temperature Behavior of the Esters by Means of Differential Scanning Calorimetry (DSC)

Instrument: DSC820 from Mettler Toledo
Analysis Conditions:
Temperature range: −100 to 250° C.
Heating rate: 10 K/min
Initial mass: about 10-11 mg
Crucible: Standard aluminum crucible with holes in the lid
Flushing gas: N2

Result: Whereas the 2-EH ester II (comparative example) shows a melting signal above 0° C., i.e., is present in solid form already above the freezing point, the isononyl ester I of the invention underwent glasslike solidification at about −80° C. In the DSC thermogram, there are no melting signals apparent, but instead only a glass transition point at about −80° C. It can therefore be assumed that the ester I of the invention does not become solid even at low temperatures, but instead remains flowable and pumpable.

Example 4

Preparation of Plastisols

The advantageous properties achievable with the esters of the invention are to be shown below in plastisols and semi-finished products obtainable from them. The initial masses used of the components for the various plastisols are indicated in table 2 below.

TABLE 2

| Formulas [all figures in phr (= parts by mass per 100 parts by mass of PVC)] | | | |
| --- | --- | --- | --- |
| | Plastisol formula | | |
| | 1 | 2 | 3 |
| Emulsion PVC (Vestolit B 7021 Ultra from Vestolit GmbH) | 100 | 100 | 100 |
| Diisononyl furan-2,5-dicarboxylate I (inventive) | 50 | | |
| Di-2-ethylhexyl furan-2,5-dicarboxylate II (comparative example) | | 50 | |
| DINP (VESTINOL 9 from Evonik Oxeno GmbH, comparative example) | | | 50 |
| Epoxidized soybean oil (Drapex 39, from Chemtura) | 3 | 3 | 3 |
| Ca/Zn stabilizer (Mark CZ 149, from Chemtura) | 2 | 2 | 2 |

The liquid constituents were weighed out before the solid constituents into a suitable PE beaker. Using a spatula, the mixture was stirred in by hand to leave no unwetted powder. The mixing beaker was then fastened into the clamping device of a dissolver stirrer. The sample was homogenized using a mixer disk.

The rotary speed of 330 rpm was increased to 2000 rpm, and stirring was continued until the temperature on the digital display of the thermal sensor reached 30.0° C. This ensured that the plastisol was homogenized with a defined energy input. The plastisol thereafter was immediately temperature-conditioned at 25.0° C.

Example 5

Measurement of Plastisol Viscosity

The viscosities of the plastisols prepared in example 4 were measured using a Physica MCR 101 rheometer (from Paar-Physica), controlled via the associated Rheoplus Software, as follows.

The plastisol was stirred once again with a spatula in the stock vessel, and was subjected to measurement in the Z3 measuring system (DIN 25 mm) in accordance with the operating instructions. Measurement ran automatically at 25° C. via the above-mentioned software. The following procedures were activated:

A preliminary shear of 100 s$^{-1}$ for a period of 60 s, during which no measured values were recorded (stabilization with respect to thixotropic effects).

An isothermal decreasing ramp, starting at a shear rate of 200 s$^{-1}$ down to 0.1 s$^{-1}$, divided into a logarithmic series with 30 steps each with a measurement point duration of 5 s.

The measurement data were processed automatically after measurement by the software. The parameter produced was the viscosity as a function of the shear rate. In order to capture changes in plastisol viscosity during plastisol storage (also: "plastisol aging"), the measurements were carried out in each case after 2 hours, 24 hours, and 7 days. Between these time points, the plastisols were stored at 25° C.

The table below lists the corresponding viscosity values obtained after the storage times indicated in each case, for a shear rate of 100 s$^{-1}$ as an example.

TABLE 3

Plastisol viscosities at a shear rate of 100 s$^{-1}$

| Plastisol No. | Plasticizer used | Viscosity after 2 h in Pa · s | Viscosity after 24 h in Pa · s | Viscosity after 7 days in Pa · s | Percentage increase in % |
|---|---|---|---|---|---|
| 1 | Diisononyl furan-2,5-dicarboxylate I (inventive) | 10.3 | 10.6 | 11.6 | 13 |
| 2 | Di-2-ethylhexyl furan-2,5-dicarboxylate II (comparative example) | 9.0 | 9.4 | 11.1 | 23 |
| 3 | DINP (comparative example) | 5.9 | 6.14 | 6.5 | 10 |

The isononyl esters I of the invention exhibit much smaller increases in plastisol viscosity over time as compared with the 2-ethylhexyl esters II. The viscosity level of the PVC plastisol of the invention, which is higher by comparison with the standard plasticizer DINP in the present formulation, can be lowered, as the skilled person is aware, in (optimized) formulations and/or other compositions by means of suitable measures such as, for example, an increase in the overall quantity of plasticizer, the addition of additional plasticizers with a lower intrinsic viscosity, the addition of rheological additives (e.g., dispersing additives or other surface-active substances) and/or the addition of (co-)solvents.

Example 6

Measurement of Gelling Rate

The gelling behavior of the plastisols was investigated in the Physica MCR 101 in oscillation mode, using a plate/plate measuring system (PP25), which was operated under shear rate control. An additional temperature-conditioning hood was fitted to the instrument in order to achieve homogeneous heat distribution and a uniform sample temperature.

The Parameters Set were as Follows:
Mode: Temperature gradient
　Start temperature: 25° C.
　End temperature: 180° C.
　Heating/cooling rate: 5° C./min
　Oscillation frequency: 4-0.1 Hz ramp, logarithmic
　Circular frequency omega: 10 1/s
　Number of measurement points: 63
　Measurement point duration: 0.5 min
　Automatic gap adjustment F: 0 N
　Constant measurement point duration
　Gap width 0.5 mm
Measurement Procedure:

One drop of the plastisol formula under measurement was applied with the spatula, without any air bubbles, to the bottom plate of the measuring system. In the course of this operation it was borne in mind that, after the measuring system has been brought together, some plastisol could swell uniformly out of the measuring system (not more than about 6 mm all round). Then the temperature conditioning hood was positioned over the sample, and measurement was commenced.

The parameter determined was the complex viscosity of the plastisol as a function of the temperature. Because a defined temperature is achieved in a timespan (determined by the heating rate of 5° C./min), not only the gelling temperature but also an indication of the gelling rate of the system measured is obtained. Onset of the process of gelling was evident from a sudden sharp increase in the complex viscosity. The earlier the onset of this increase in viscosity, the better the gelability of the system. For a comparison, interpolation of the curves for each plastisol was used to determine the temperature at which a complex viscosity of 1000 Pa·s was reached.

In this procedure, the values obtained are those set out in table 4:

TABLE 4

| | Gelling behavior | | |
|---|---|---|---|
| | Plastisols from example 4 | | |
| | 1 (inventive) | 2 (comparative example) | 3 (Comparative example) |
| Temperature at viscosity of 1000 Pa · s | 85° C. | 80.5° C. | 88.5° C. |

It is clearly apparent that the furandicarboxylic esters gel earlier (i.e., at lower temperatures) than the corresponding phthalates.

Example 7

Measurement of the Shore Hardness of Castings

Shore hardness A is a measure of the plasticity of a specimen. The further a standardized needle can be made to penetrate into the specimen in a defined measurement time, the lower the measurement value. The plasticizer with the highest efficiency gives the lowest Shore hardness value for a given quantity of plasticizer. Conversely, in the case of highly efficient plasticizers, it is possible to make a certain saving in the proportion in the formula, and in many cases this translates to lower costs for the processor.

For the determination of the Shore hardnesses, the plastisols prepared in accordance with example 4 were poured into circular casting molds having a diameter of 42 mm. The plastisols in the molds were then gelled in a forced-air drying oven at 200° C. for 30 minutes, demolded after cooling, and stored at 25° C. for at least 24 hours prior to measurement. The thickness of the castings was approximately 12 mm.

The measurements themselves were carried out in accordance with DIN 53 505 using a Shore A measuring instrument from Zwick-Roell, the measurement value being read off after 3 seconds in each case. On each specimen, three different measurements were carried out at different points (not in the marginal zone), and the average was recorded in each case.

Table 5 lists the measurement values obtained.

TABLE 5

Shore A hardnesses

| | Plastisols from example 4 | | |
|---|---|---|---|
| | 1 (inventive) | 2 (comparative example) | 3 (comparative example) |
| Shore hardness A | 78 | 75 | 80 |

The examples listed demonstrate that the diisononyl ester of the furandicarboxylic acid I, of the invention, has the decisive advantage over the closest prior art, the bis(2-ethylhexyl) furan-2,5-dicarboxylate II, of noncrystallization. As compared with the corresponding phthalate DINP, there are improvements, in some cases significantly so, in the plasticizing effect and in the gelling rate.

Example 8

Use of the Furandicarboxylic Esters of the Invention in PVC Topcoat Formulation (Plastisol) Together with Diisononyl Terephthalate (DINT)—Preparation of the Topcoat Plastisols The plastisols were prepared in accordance with example 4 but with a modified formula. The initial masses used for the components of the various plastisols are indicated in the table below (table 6).

TABLE 6

Formulas [All figures in phr (= parts by mass per 100 parts by mass of PVC)]

| | Plastisol formula | | |
|---|---|---|---|
| | 1 | 2 | 3 |
| Microsuspension PVC K70 (VESTOLIT B7021 Ultra, from Vestolit) | 100 | 100 | 100 |
| Diisononyl furan-2,5-dicarboxylate; preparation by example 2 (inventive) | 10 | 15 | |
| Diisononyl (ortho)phthalate [DINP] (VESTINOL 9 from Evonik Oxeno GmbH, comparative example) | | | 50 |
| Diisononyl terephthalate (laboratory product, preparation by DE 102008006400A1/example 1) | 40 | 35 | |
| Epoxidized soybean oil (Drapex 39; Chemtura/Galata) | 3 | 3 | 3 |
| Calcium/zinc stabilizer (Mark CZ 149, from Chemtura/Galata) | 2 | 2 | 2 |

Example 9

Determination of the Plastisol Viscosity of the Topcoat Plastisols (from Example 8) Comprising the Furandicarboxylic Esters of the Invention and Diisononyl Terephthalate after a Storage Period of 24 h (at 25° C.).

The viscosities of the plastisols prepared in example 8 were measured using a Physica MCR 101 rheometer (from Paar-Physica), in accordance with the procedure described in example 5. The results are shown in the table below (table 7) by way of example for the shear rates of 100/s, 10/s, 1/s, and 0.1/s.

TABLE 7

Shear viscosity of the plastisols from example 8 after 24 h storage at 25° C.

| | Plastisol formula (from example 8) | | |
|---|---|---|---|
| | 1* | 2* | 3** |
| Shear viscosity at shear rate = 100/s [Pa * s] | 8 | 8 | 6 |
| Shear viscosity at shear rate = 10/s [Pa * s] | 3.6 | 3.5 | 3.1 |
| Shear viscosity at shear rate = 1/s [Pa * s] | 2.7 | 2.9 | 2.8 |
| Shear viscosity at shear rate = 0.1/s [Pa * s] | 3.1 | 3.4 | 3.7 |

**= Comparative example
*= Inventive

In the range of low shear rates, the plastisols comprising the furandicarboxylic esters of the invention are situated in terms of their shear viscosity at or below the level of the analogous DINP plastisol. At higher shear rates, the shear viscosities of the plastisols of the invention are situated only slightly above the shear viscosity of the analogous DINP plastisol. By blending diisononyl terephthalate with the furandicarboxylic esters of the invention, therefore, it is possible to prepare plastisols which have processing properties similar to those of DINP plastisols but at the same time do not contain ortho-phthalates, and which are based on renewable raw materials.

Example 10

Use of the Furandicarboxylic Esters of the Invention in Thermally Expandable Plastisols (Flooring) Together with Fast Gellers—Preparation of the Plastisols The plastisols were prepared as in example 4 but with a modified formula. The initial masses used of the components for the various plastisols are indicated in the table below (table 8).

TABLE 8

Formulas of thermally expandable plastisols
[All figures in phr (= parts by mass per 100 parts by mass of PVC)]

| | Plastisol formula | | | | | |
|---|---|---|---|---|---|---|
| | 1** | 2* | 3* | 4* | 5* | 6* |
| Vinnolit MP 6852 | 100 | 100 | 100 | 100 | 100 | 100 |
| Vestinol 9 | 50 | 12.5 | | | | |
| Citrofol BII | | | 12.5 | | | |
| Mesamol II | | | | 12.5 | | |
| Jayflex MB10 | | | | | 12.5 | |
| Eastman DBT | | | | | | 12.5 |
| DINFDC | | 37.5 | 37.5 | 37.5 | 37.5 | 37.5 |
| Unifoam AZ Ultra 7043 | 3 | 3 | 3 | 3 | 3 | 3 |
| ZnO | 0.7 | 0.7 | 0.7 | 0.7 | 0.7 | 0.7 |

**= Comparative example
*= Inventive

The compounds and substances used are explained below:
Vinnolit MP 6852: Microsuspensions PVC (homopolymer) with K value (as per DIN EN ISO 1628-2) of 68; from Vinnolit GmbH & Co KG.
Vestinol 9: Diisononyl (ortho)phthalate [DINP], plasticizer; from Evonik Oxeno GmbH.
Citrofol BII: Acetyl tributyl citrate, plasticizer with fast gelling; from Jungbunzlauer AG.
Mesamol II: Alkylsulfonic ester of phenol; plasticizer with fast gelling; from Lanxess AG.
Jayflex MB10: Isodecyl benzoate; plasticizer with fast gelling; from ExxonMobi Chemicals.
Eastman DBT: Dibutyl terephthalate; plasticizer with fast gelling; from Eastman Chemical Co.
DINFDC: diisononyl furan-2,5-dicarboxylate of the invention; preparation as per example 2.
Unifoam AZ Ultra 7043: Azodicarbonamide; thermally activatable blowing agent; from Hebron S.A.
ZnO: Zinc oxide; decomposition catalyst for thermal blowing agent; reduces the inherent decomposition temperature of the blowing agent; active zinc oxide; from Lanxess AG.

Example 11

Determination of the Viscosity of the Thermally Expandable Plastisols (from Example 10) Comprising the Furandicarboxylic Esters of the Invention and Diisononyl (Ortho)Phthalate and/or Fast Gellers after a Storage Time of 24 h (at 25° C.)

The viscosities of the plastisols prepared in example 10 were measured using a Physica MCR 101 rheometer (from Paar-Physica), in accordance with the procedure described in example 5. The results are set out in the table below (table 9) by way of example for the shear rates of 100/s, 10/s, 1/s and 0.1/s.

TABLE 9

Shear viscosity of the plastisols from example
8 after 24 h storage at 25° C.

| | Plastisol formula (as per example 10) | | | | | |
|---|---|---|---|---|---|---|
| | 1** | 2* | 3* | 4* | 5* | 6* |
| Shear viscosity at shear rate = 100/s [Pa * s] | 6.1 | 10.9 | 11.5 | 11.2 | 6.1 | 11 |
| Shear viscosity at shear rate = 10/s [Pa * s] | 4.5 | 7.8 | 8.5 | 10.2 | 4.7 | 9.2 |
| Shear viscosity at shear rate = 1/s [Pa * s] | 5.2 | 8.5 | 9.6 | 10.7 | 5.7 | 11.7 |
| Shear viscosity at shear rate = 0.1/s [Pa * s] | 8.2 | 12.9 | 15.2 | 15.7 | 9.5 | 22.5 |

**= Comparative examples
*= Inventive

Through the choice of the fast geller it is possible to adjust the viscosity of the plastisol in a deliberate way, with the combination of diisononyl furandicarboxylate of the invention and alkyl benzoate in the present case (plastisol formula 5) leading to a rheological behavior similar to that found when using the universal plasticizer diisononyl (ortho)phthalate. In other words, plastisols of the invention are provided which can be used under similar processing conditions (e.g., application rates) as the current standard plasticizer DINP, but do not (have to) contain orthophthalates and are based at least partly on renewable raw materials.

Example 12

Production of Foam Sheets from and Determination of the Expansion and Foaming Behavior of the Thermally Expandable Plastisols (from Example 10) Comprising the Furandicarboxylic Esters of the Invention and Diisononyl(Ortho)Phthalate and/or Fast Gellers at 200° C.

Foaming behavior was determined using a quick thickness gauge (suitable for plasticized PVC measurements) to an accuracy of 0.01 mm. For sheet production, a blade gap of 1 mm was set on the roll blade of a Mathis Labcoaters (manufacturer: W. Mathis AG). This blade gap was checked with a feeler gauge and adjusted if necessary. The plastisols prepared in example 10 were coated by means of the roll blade of the Mathis Labcoater onto a release paper (Warran Release Paper; from Sappi Ltd) stretched flat in a frame. In order to be able to calculate the percentage foaming, an incipiently gelled and unfoamed sheet was produced first of all. The thickness of this sheet with the stated blade gap was 0.74 mm. The thickness was measured at three different points on the sheet. Subsequently, again with the/in the Mathis Labcoater, the foamed sheets (foams) were produced with four different oven residence times (60 s, 90 s, 120 s, and 150 s). After the foams had cooled, the thicknesses were likewise measured at three different points. The average value of the thicknesses, and the original thickness of 0.74 mm, were needed for the calculation of the expansion (example: (foam thickness-original thickness)/original thickness*100%=expansion). The results are shown in the table below (table 10).

TABLE 10 expansion rates of the polymer foams prepared from the thermally expandable plastisols (from example 10) with different oven residence times in the Mathis Labcoater at 200° C.

| | Plastisol formula (from example 10) | | | | | |
|---|---|---|---|---|---|---|
| | 1** | 2* | 3* | 4* | 5* | 6* |
| Expansion after 60 s [%] | 19 | 3 | 0 | 42 | 35 | 28 |
| Expansion after 90 s [%] | 386 | 386 | 400 | 427 | 386 | 400 |
| Expansion after 120 s [%] | 454 | 474 | 481 | 501 | 474 | 508 |
| Expansion after 150 s [%] | 488 | 508 | 515 | 522 | 495 | 528 |

**= Comparative example
*= Inventive

The plastisol formulas of the invention which comprise diisononyl furandicarboxylates expand much quicker than with the diisononyl phthalate plasticizer used alone in the comparative example (plastisol formula 1). Through the deliberate use of particular fast gellers such as certain citric esters, for example (plastisol formula 3), PVC plastisols can be prepared which on the one hand can be subjected to thermal pretreatment (e.g., preliminary gelling in the case of a multilayer construction), without exhibiting measurable expansion at this early point, but on the other hand subsequently expand all the more quickly. Through the selection of different plasticizer combination partners, it is also possible to prepare PVC plastisols which (like plastisol formulas 4 and 5, for example) exhibit strong expansion right at the start, and so permit a significantly shorter overall processing time as compared with the current standard plasticizer DINP. PVC plastisols are provided, accordingly, which exhibit a wide spectrum of different processing possibilities.

Example 13

Determination of the Gelling Behavior of Thermally Expandable Plastisols (from Example 10) Comprising the Furandicarboxylic Esters of the Invention and Diisononyl(Ortho)Phthalate and/or Fast Gellers The gelling behavior of the thermally expandable plastisols prepared in example 10 was investigated in the Physica MCR 101 in oscillation mode using a plate/plate measuring system (PP25) which was operated under shear rate control, in accordance with the procedure described in example 6. The parameter determined was the complex viscosity of the plastisol as a function of the temperature, with constant heating rate (i.e., gelling curve). Onset of the gelling process is apparent from a sudden sharp increase in the complex viscosity. The earlier the onset of this increase in viscosity, the faster the gelling of the corresponding plastisol. By interpolation for each plastisol, the measurement curves obtained were used to determine the temperatures at which a complex viscosity of 1000 Pa·s and 10 000 Pa·s was reached. In addition, a tangent method was used to determine the maximum plastisol viscosity achieved in the present experimental system, and the temperature from which maximum plastisol viscosity occurs was determined by the dropping of a perpendicular. The results are shown in the table below (table 11).

TABLE 11

Key data, determined from the gelling curves (viscosity curves), of the gelling behavior of the thermally expandable plastisols prepared in example 10

| | Plastisol formula (from example 10) | | | | | |
|---|---|---|---|---|---|---|
| | 1** | 2* | 3* | 4* | 5* | 6* |
| Attainment of a plastisol viscosity of 1000 Pa * s at [° C.] | 80 | 80 | 78 | 78 | 77 | 74 |
| Attainment of a plastisol viscosity of 10 000 Pa * s at [° C.] | 84 | 84 | 82 | 82 | 80 | 77 |
| Maximum plastisol viscosity [Pa * s] | 42000 | 41000 | 52500 | 53000 | 43000 | 61000 |
| Temperature at attainment of maximum plastisol viscosity [° C.] | 92 | 90 | 88 | 88 | 88 | 86 |

**= Comparative example
*= Inventive

Through the choice of the fast geller it is not only possible, as expected, to adjust the gelling rate and also the gelling temperature, but also, to a surprisingly high degree, the maximum viscosity of the fully gelled plastisol (maximum plastisol viscosity), and hence the physical properties of the PVC foam produced through the thermal expansion. Accordingly, thermally expandable PVC plastisols are provided which on the one hand gel substantially more quickly than plastisols produced using the current standard plasticizer DINP alone, but on the other hand can also be processed to foams having significantly higher viscosity, and significantly higher strength and/or elasticity.

Example 14

Use of the Furandicarboxylic Esters of the Invention Together with Other Plasticizers in Dryblends—Production of the Dryblends The advantageous properties achievable with the esters of the invention will be demonstrated below by way of example for dry mixtures, known as dryblends, and for the semifinished products obtainable from these blends. The formulas prepared are shown in the table below (table 12).

TABLE 12

Formulas of the dryblends
[All figures in phr (= parts by mass per 100 parts by mass of PVC)]

| | Dryblend | | | | | | |
|---|---|---|---|---|---|---|---|
| | 1** | 2* | 3* | 4* | 5* | 6* | 7* |
| Solvin S 271 PC | 100 | 100 | 100 | 100 | 100 | 100 | 100 |
| Vestinol 9 | 50 | 37.5 | | | | | |
| DEHT | | | 37.5 | | | | |
| DINT | | | | 37.5 | | | |
| DINCH | | | | | 37.5 | | |
| GSS | | | | | | 37.5 | |
| Polysorb ID 37 | | | | | | | 37.5 |
| DINFDC | | 12.5 | 12.5 | 12.5 | 12.5 | 12.5 | 12.5 |

TABLE 12-continued

Formulas of the dryblends
[All figures in phr (= parts by mass per 100 parts by mass of PVC)]

| | Dryblend | | | | | | |
|---|---|---|---|---|---|---|---|
| | 1** | 2* | 3* | 4* | 5* | 6* | 7* |
| Drapex 39 | 3 | 3 | 3 | 3 | 3 | 3 | 3 |
| Mark BZ 561 | 2 | 2 | 2 | 2 | 2 | 2 | 2 |
| Calcium stearate | 0.4 | 0.4 | 0.4 | 0.4 | 0.4 | 0.4 | 0.4 |

**= Comparative example
*= Inventive

The compounds and substances used are explained below:

Solvin S 271 PC: Suspension PVC having a K value (determined to DIN EN ISO 1628-2) of 71; from SOLVIN S.A.

Vestinol 9: Diisononyl (ortho)phthalate [DINP], plasticizer; from Evonik Oxeno GmbH.

DEHT: Di(2-ethylhexyl) terephthalate; "Eastman 168"; plasticizer; from Eastman Chemical.

DINT: Diisononyl terephthalate (Laboratory product, prepared as per DE 102008006400A1/example 1)

DINCH: Di(isononyl) cyclohexanedicarboxylate; Hexamoll DINCH; plasticizer; from BASF AG.

GSS: Octadecanoic acid 12-(acetyloxy)-2,3-bis(acetyloxy)propyl ester; glycerol triester produced on the basis of castor oil; "Grindsted Soft'n Safe"; plasticizer; from Danisco A/S.

Polysorb ID 37: Isosorbide di(octanoic acid)ester; plasticizer; from Roquette Freres.

DINFDC: Diisononyl furan-2,5-dicarboxylate of the invention; preparation as per example 2.

Drapex 39: Epoxidized soybean oil; Costabilizer & Coplasticizer; from Chemtura/Galata.

Mark BZ 561: Barium/zinc stabilizer; from Chemtura/Galata.

Calcium stearate: Calcium salt of stearic acid; lubricant.

The dryblends were produced in a Brabender planetary mixer. A thermostat heated the mixing vessel of the planetary mixer to a constant temperature of 90° C. Via the "Winmix" software, the following parameters were set on the Brabender planetary mixer:

Rotary speed program: Active

Profile: Rotary speed 50 rpm; hold time: 9 min; increase time: 1 min

Rotary speed 100 rpm; hold time: 20 min

Kneader temperature: 88° C.

Measuring range: 2 Nm

Attenuation: 3

The temperature in the mixing vessel was 88° C. After the planetary mixer had carried out self-calibration, the solid constituents were supplied to the mixing vessel. The program was commenced and the powder mixture was stirred in the mixing vessel for 10 minutes and brought to a controlled temperature before the liquid constituents were added. The mixture was stirred in the planetary mixer for a further 20 minutes. After the end of the program, the completed dryblend (powder) was discharged. The transferred torque/time diagram was evaluated by the Brabender software. Following the addition of the liquid constituents, a distinct rise is evident in the curve. Only when the curve falls off significantly again is the incorporation of plasticizer complete. The time difference between these two points is the plasticizer incorporation time (dryblend time). The maximum torque is evaluated automatically by the program. Plasticizer incorporation and the maximum torque determined when producing the dryblends are shown in table 13.

TABLE 13

Time required for the incorporation of the liquid formula components by the preheated PVC (plasticizer incorporation) and maximum torque determined during dryblend production

| | Dryblend from example 14 | | | | | | |
|---|---|---|---|---|---|---|---|
| | 1** | 2* | 3* | 4* | 5* | 6* | 7* |
| Plasticizer incorporation [min.] | 4.5 | 4.2 | 4.8 | 6.2 | 5.5 | 3.7 | 3.3 |
| Maximum torque [Nm] | 1.1 | 1.1 | 1 | 1.1 | 1.1 | 1.1 | 1 |

**= Comparative example
*= Inventive

The processing speed of the blends of the invention is higher, in some cases markedly so, than that for the comparative formula with the standard plasticizer DINP; the maximum torque is comparable in all cases. Accordingly, dryblends are provided which by comparison with the current standard plasticizer DINP permit a significantly higher processing rate for a similar applied force.

Example 15

Production of Milled Sheets and Press-Molded Plates from the Dryblends (from Example 14) Comprising the Furandicarboxylic Esters of the Invention Together with Other Plasticizers Production of the Milled Sheets The milled sheets were produced on a W150 AP calender from Collin.

The parameters set on the calender were as follows:
Roll temperature: 165° C.
Roll nip: 0.5 mm
Rolling time: 5 min
Five-stage program for producing the milled sheet When the roll temperature was reached, the roll nip was calibrated. At the start of the measurement, the roll nip was set to 0.2 mm. 160 grams of a dryblend (from example 14) were weighed out in each case and placed into the roll nip, with the rolls stationary. The program was commenced. The rolls started with a rotary speed of 5 rpm and a friction of 20%. After about 1 minute, plasticization was very largely at an end, and the roll nip was enlarged to 0.5 mm. Threefold homogenization took place by means of an automatic turnover unit on the calender. After 5 minutes, the milled sheet was removed from the roll and cooled.

Production of the Press-Molded Plates

Press-molded plates were produced on a laboratory press from Collin. The prefabricated milled sheets (see above) were used for producing the press-molded plates. The lateral margins of the milled sheets were removed by means of a cutting machine, after which the milled sheet was cut into sections measuring approximately 14.5×14.5 cm. For molded plates 1 mm thick, two milled-sheet sections were placed into the 15×15 cm stainless steel pressing frame.

The parameters set out on the laboratory press were as follows:

Three-phase program:
Phase 1: Both platens 165°; press platen pressure: 5 bar; phase time: 60 seconds.
Phase 2: Both platens 165°; press platen pressure: 200 bar; phase time: 120 seconds.
Phase 3: Both platens 40°; press platen pressure: 200 bar; phase time: 270 seconds.

The excess press exudate was removed after the press-molded plates had been produced.

Example 16

Determination of the Plasticizing Effect and Plasticizer Efficiency on Press-Molded Plates Produced from the Dryblends Comprising the Furandicarboxylic Esters of the Invention Together with other Plasticizers, by Determination of the Shore Hardness (Shore A and D)

The Shore hardness is a measure of the plasticity of a specimen. The further a standardized needle can be made to penetrate into the specimen in a defined measurement time, the lower the measurement value. For a given quantity of plasticizer, the plasticizer with the greatest efficiency produces the lowest value for the Shore hardness. Since in practice formulations/formulas are frequently set to or optimized for a defined Shore hardness, accordingly, it is possible in the case of very efficient plasticizers to make a saving in the formula of a certain fraction, this implying a reduction in costs for the processor.

The hardness measurements were carried out in accordance with DIN 53 505 using a Shore A and a Shore D measuring instrument from Zwick-Roell, the measurement value being read off after 3 seconds in each case. On each specimen (produced as per example 15), measurements were carried out at three different points, and an average was formed. The results of the determination of hardness are summarized in table 14.

TABLE 14

Shore A and Shore D hardnesses of press-molded plates produced (according to example 15) from the dryblends (from example 14) comprising the furandicarboxylic esters of the invention together with other plasticizers

| | Dryblend from example 14 | | | | | | |
|---|---|---|---|---|---|---|---|
| | 1** | 2* | 3* | 4* | 5* | 6* | 7* |
| Shore A | 85 | 85 | 86 | 88 | 86 | 83 | 85 |
| Shore D | 28 | 28 | 28 | 30 | 28 | 26 | 27 |

**= Comparative example
*= Inventive

Blending different standard plasticizers with the furandicarboxylic esters of the invention in dryblends produces a plasticizer efficiency which is similar to or better than that of DINP (standard plasticizer). In addition, dryblends are provided which as compared with the DINP presently in use as a universal plasticizer, exhibit a significantly improved efficiency and may therefore lead in particular to lower formula costs.

Example 17

Determination of the Water Absorption and Leaching Behavior on Press-Molded Plates (Semifinished Products) Produced from the Dryblends Comprising the Furandicarboxylic Esters of the Invention Together with Other Plasticizers Water absorption and leaching behavior are two key criteria in assessing the quality of semifinished products produced on the basis of PVC dryblends. If a semifinished PVC product absorbs water to a substantial extent, this results on the one hand in a change in its physical properties, and on the other hand in a change in its visual appearance (e.g., hazing). A high level of water absorption, accordingly, is generally undesirable. The leaching behavior is an additional criterion of the permanence of the formulation constituents under service conditions (e.g., in floorcoverings or roofing sheets). This applies particularly to stabilizers, plasticizers and/or their ingredients, since a reduction in concentration of these formula constituents in the semifinished product may not only impair the physical properties but also dramatically reduce the lifetime of the semifinished products.

Production of the Test Specimens

For each sample/dryblend, 3 circles (each 10 cm$^2$) were cut with the aid of a circle cutter from the press-molded plates (produced as per example 15). The circles were perforated. Prior to water storage, the circles were stored in a desiccator furnished with drying agent (KC drying pearls) at 25° C. for 24 hours. The original weight (initial mass) was determined on an analytical balance to an accuracy of 0.1 mg. The circles were then stored in a shaking bath filled with fully demineralized water, at a temperature of 30° C., below the water surface, with suitable sample holders, for 24 hours, and were moved continuously. After the storage, the circles were taken from the water bath, dried off, and weighed (weight after 24 h). The weighed circles were placed back in the water bath and after 7 days, weighed again in the dried-off state (weight after 7 days). After the second weighing, the cycles were again stored in a desiccator furnished with drying agent (KC drying pearls) at 25° C. for 24 hours, and then weighed once again (final mass=weight after drying). The changes in weight were calculated as percentages, and are shown in table 15.

TABLE 15

Water absorption and leaching behavior determined on test specimens produced from press-molded plates (as per example 15) produced from the dryblends (from example 14) comprising the furandicarboxylic esters of the invention together with other plasticizers

| | Dryblend from example 14 | | | | | | |
|---|---|---|---|---|---|---|---|
| | 1** | 2* | 3* | 4* | 5* | 6* | 7* |
| Weight change after 1 day [ma %] | +0.26 | +0.27 | +0.24 | +0.24 | +0.3 | +0.4 | +0.06 |
| Weight change after 7 days [ma %] | +0.33 | +0.34 | +0.34 | +0.38 | +0.41 | +0.35 | −0.57 |
| Weight change after drying [ma %] | −0.16 | −0.14 | −0.17 | −0.13 | −0.16 | −0.35 | −1.16 |

**= Comparative example
*= Inventive

The test specimens comprising the furandicarboxylic esters are similar in terms of their water storage behavior to the test specimen containing solely the standard plasticizer DINP. The water absorption is extremely low, which is an advantage especially for calendered floorcoverings but also for roofing sheets. The loss of mass through leaching is also within narrow limits, with the exception of the mixture of isosorbide ester Polysorb ID 37 and diisononyl furandicarboxylate. Accordingly, dryblends and semifinished products producible therefrom are provided which are distinguished by low water absorption and low leaching characteristics, and are therefore ideally suited also for use in areas with continual or frequent water contact.

Example 18

Determination of the Tensile/Elongation Properties on Press-Molded Plates (Semifinished Products) Produced from Dryblends Comprising the Furandicarboxylic Esters of the Invention Together with Other Plasticizers Tensile strength and elongation at break are physical properties which play an important part especially for semifinished products under mechanical load. This mechanical loading may occur both during the process of producing the semifinished product and during its service. Preference (particularly in the roofing sheet sector) is given in the majority of cases to materials which exhibit a high tensile strength with moderate elongation.

For the tensile tests, standardized "S-2" test bars were punched from the press-molded sheets produced as per example 15. The tensile tests took place in accordance with DIN 53504 on a "Z 1445" tensile tester from Zwick.

The test parameters set were as follows:
Test conditions: 23° C., 50% rh
Initial force: 0.5 N
Initial force speed: 5 mm/min
Testing speed: 100 mm/min For the determination of the tensile strength and the elongation at break, 5 measurements were carried out per sample. The averaged measurement values have been entered in the table below (table 16).

TABLE 16

Tensile properties determined in accordance with DIN 53504 on S2 test specimens produced from press-molded plates (as per example 15) produced from the dryblends (from example 14) comprising the furandicarboxylic esters of the invention together with other plasticizers

| | Dryblend from example 14 | | | | | | |
|---|---|---|---|---|---|---|---|
| | 1** | 2* | 3* | 4* | 5* | 6* | 7* |
| Tensile strength [MPa] | 23.7 | 23.9 | 25.3 | 25.6 | 23.8 | 25.0 | 26.6 |
| Elongation at break [%] | 285 | 300 | 305 | 300 | 290 | 325 | 320 |

**= Comparative example
*= Inventive

By using the mixtures of the invention it is possible to achieve a considerable increase in the tensile strength by comparison with the pure DINP (standard plasticizer). There are no restrictions here on the flexibility of the material; instead, the elongation at break is in fact slightly increased. Accordingly, dryblends and semifinished products producible therefrom are provided which are distinguished by a high tensile strength in conjunction with high flexibility and high dimensional stability, and which are therefore suitable also for use under high mechanical load (for bracing, among other uses).

Example 19

Use of the Furandicarboxylic Esters of the Invention in Protection Compounds (e.g., Underbody Protection/UBP)—Preparation of the UBP Plastisols)

The advantageous properties achievable with the esters of the invention will be demonstrated below on UBP plastisols (protection compounds). The plastisols were prepared as in example 4 but with a modified formula. The initial masses used for the components of the various plastisols can be seen from the table below (table 17).

TABLE 17

Formulas of the UBP protection compounds (plastisols)
[All figures in phr (= parts by mass per 100 parts by mass of PVC)]

| | Plastisol formula | |
|---|---|---|
| | 1* | 2** |
| Emulsion PVC with K value of 70 (VESTOLIT E 7031, from Vestolit) | 100 | 100 |
| Diisononyl furan-2,5-dicarboxylate (inventive) | 130 | |
| DINP (VESTINOL 9 from Evonik Oxeno GmbH, comparative example) | | 130 |
| Coated calcium carbonate (Socal 312, from Solvay Chemicals) | 70 | 70 |
| White lime DIN EN 459-1/CL-Q-fine lime (Precal 30 S, from Schäfer-Krusemark) | 5 | 5 |
| Adhesion promoter (Nouribond 323, from Air Products) | 3 | 3 |
| Zinc oxide (zinc oxide active; from Lanxess AG) | 1 | 1 |
| Aliphatic solvent (Shellsol D70; from Shell Chemicals) | 5 | 5 |

**= Comparative example
*= Inventive

Example 20

Determination of the Plastisol Viscosity of UBP Plastisols Comprising the Furandicarboxylic Esters of the Invention after a Storage Time of 2 h (at 25° C.)

Protection compounds, particularly those used in the vehicle underbody protection area, are required to meet different viscosity requirements according to the prevailing shear rate. Accordingly, during application, which is generally done under high shear rates by spraying, the protection compounds are to flow very easily and exhibit, on the treated surface, a homogeneous spray pattern and good leveling. After application (i.e., in the absence, very largely, of any shearing force), in contrast, they are to have a high viscosity and to exhibit little post-application flow.

The viscosities of the plastisols prepared in example 19 were measured using a Physica MCR 101 rheometer (from Paar-Physica), in accordance with the procedure described in example 5, after the pastes had been temperature-conditioned for a time of 2 hours at 25° C. The results are shown in the table below (table 18) by way of example for the shear rates 100/s, 10/s, 1/s, and 0.1/s.

TABLE 18

Shear viscosity of the plastisols from example 19 after 2 h of storage at 25° C.

| | Plastisol formula from example 19 | |
|---|---|---|
| | 1* | 2** |
| Shear viscosity at shear rate = 100/s [Pa * s] | 7.2 | 7.2 |
| Shear viscosity at shear rate = 10/s [Pa * s] | 50 | 54.5 |
| Shear viscosity at shear rate = 1/s [Pa * s] | 423 | 437 |
| Shear viscosity at shear rate = 0.1/s [Pa * s] | 1590 | 1150 |

**= Comparative example
*= Inventive

In comparison with DINP (standard plasticizer, plastisol formula 2), the UBP paste/UBP plastisol based on the furandicarboxylic ester mixture of the invention (plastisol formula 1) also has a low shear viscosity at high shear rates, whereas at low shear rates it is well above the shear viscosity of the DINP paste. In application, therefore, with the same processing properties, there is a clear advantage in terms of the drip resistance of the formulation. Accordingly, UBP plastisols are provided which combine excellent spraying and leveling properties with very low post-application flow.

Example 21

Determination of the Gelling Rate of UBP Plastisols Comprising the Furandicarboxylic Esters of the Invention Gelling of the UBP protection compounds must be possible within the thermal curing processes that exist in the automobile industry. On the one hand, an important factor is extremely rapid solidification of the protection compound, in order to prevent subsequent dripping, while on the other hand another important factor is a complete or near-complete gelling within an extremely short time, in order to achieve maximum protection effect. The gelling behavior of the UBP plastisols prepared in example 19 was investigated in the Physica MCR 101 in oscillation mode using a plate/plate measuring system (PP25) which was operated under shear rate control, in accordance with the procedure described in example 6.

The parameter determined was the complex viscosity of the plastisol as a function of the temperature, with constant heating rate (i.e., gelling curve). Onset of the gelling process is apparent from a sudden sharp increase in the complex viscosity. The earlier the onset of this increase in viscosity, the faster the gelling of the corresponding plastisol. By interpolation for each plastisol, the measurement curves obtained were used to determine the temperatures at which a complex viscosity of 1000 Pa·s and 10 000 Pa·s was reached. In addition, a tangent method was used to determine the maximum plastisol viscosity achieved in the present experimental system, and the temperature from which maximum plastisol viscosity occurs was determined by the dropping of a perpendicular. The results are shown in the table below (table 19).

TABLE 19

Key data, determined from the gelling curves (viscosity curves), of the gelling behavior of the UBP plastisols prepared in example 19

|  | Plastisol formula from example 19 | |
| --- | --- | --- |
|  | 1* | 2** |
| Attainment of a plastisol viscosity of 1 000 Pa * s at [° C.] | 50 | 74 |
| Attainment of a plastisol viscosity of 10 000 Pa * s at [° C.] | 75 | 110 |
| Maximum plastisol viscosity [Pa * s] | 82 000 | 13 000 |
| Temperature at attainment of maximum plastisol viscosity [° C.] | 124 | 130 |

**= Comparative example
*= Inventive

The UBP protection compound comprising the furandicarboxylic esters of the invention exhibits substantially more rapid gelling than the comparable DINP protection compound; accordingly, substantially more rapid processing or, alternatively, the use of lower processing temperatures (=energy and cost saving) is possible. The substantially higher ultimate viscosity of the UBP protection compound of the invention also points to an improved protective effect of the compound against stone chipping, for example. Accordingly, UBP plastisols are provided which by comparison with UBP plastisols based on the present standard plasticizer DINP have significantly better processing and physical properties.

Example 22

Adhesion Effect of UBP Protection Compounds Comprising the Furandicarboxylic Esters of the Invention on Standard Metal Panels Critical to the ongoing protective effect of UBP protection compounds are, among other properties, the adhesion properties of the fully gelled UBP protection compounds on the automotive bodywork panels.

For the testing of adhesion, specially coated "Cathogard" panels (BASF Coatings GmbH) were used. A doctor blade was used to coat the metal panels with the UBP plastisols from example 19. The UBP plastisols were used after a storage time of 2 hours at 25° C. For coating, the metal panels were taped off with adhesive tape so as to produce four areas with a size of approximately 7×3 cm. The plastisols were first distributed over the four areas using a spatula. Using the doctor blade, the plastisols were then coated out smoothly. Excess plastisol and the adhesive tape were removed. The coated panels were gelled in a drying oven at a temperature of 130° C. for 25 minutes.

The adhesion test was carried out after three different time conditions (2 hours/24 hours/168 hours). For the test, the areas were divided with a razor blade into a number of small areas. Then, using a special-purpose spatula, an attempt was made to detach the first area. The adhesion/detachment behavior was evaluated (see table 20). Between the tests, the fully gelled panels were stored in a temperature-conditioning cabinet at 25° C.

TABLE 20

Evaluation system for the adhesion/detachment test on the fully gelled UBP plastisols

| Evaluation | Signification |
| --- | --- |
| 1 | very good adhesion |
| 2 | good adhesion |
| 3 | satisfactory adhesion |
| 4 | adequate adhesion |
| 5 | Deficient adhesion |
| 6 | Inadequate/no adhesion |

The results of the adhesion/detachment test on the fully gelled UBP plastisols are collated in the table below (table 21).

TABLE 21

Adhesion/detachment properties of the fully gelled UBP plastisols, prepared according to example 19

|  | Plastisol formula from example 19 | |
| --- | --- | --- |
|  | 1* | 2** |
| Adhesion after 2 h storage of fully gelled sample | 3 | 3 |
| Adhesion after 24 h storage of fully gelled sample | 3 | 3 |
| Adhesion after 168 h storage of fully gelled sample | 3 | 3 |

**= Comparative example
*= Inventive

The protection compound comprising the furandicarboxylic esters of the invention therefore has the same adhesion properties as the analogous DINP protection compound. Accordingly, UBP protection compounds are provided which as well as very good processing and physical properties also exhibit good adhesion to automotive panels, and hence have a good protective effect.

The invention claimed is:

1. A mixture, comprising:
isomeric nonyl esters of a furan-2,5-dicarboxylic acid of formula I:

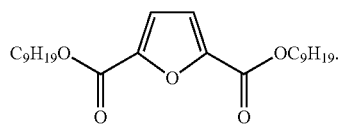

2. The mixture of claim 1, comprising at least two nonyl esters, which comprise different isomeric C9 radicals,
wherein no C9 radical in the mixture has a fraction of more than 90 mol %.

3. A process for preparing the mixture of claim 1, the process comprising:
contacting furan-2,5-dicarboxylic acid with a mixture comprising isomeric C9 alcohols in the presence of at least one catalyst selected from the group consisting of a Brønsted acid and a Lewis acid, thereby liberating water;
wherein the isomeric C9 alcohols are in a molar excess of up to 50%.

4. A process for preparing the mixture of claim 1, the process comprising:
a) chlorinating furan-2,5-dicarboxylic acid, to obtain furan-2,5-dicarbonyl chloride;
b) isolating and purifying the furan-2,5-dicarbonyl chloride; and then
c) contacting the furan-2,5-dicarbonyl chloride with a mixture comprising isomeric C9 alcohols, thereby liberating hydrogen chloride.

5. A process for preparing the mixture of claim 1, the process comprising:
contacting dimethyl furan-2,5-dicarboxylate with a mixture comprising isomeric C9 alcohols, in the presence of at least one catalyst selected from the group consisting of a Brønsted acid and a Lewis acid, thereby liberating methanol.

6. A composition, comprising:
the mixture of claim 1; and
at least one plasticizer selected from the group consisting of an alkyl benzoate, a dialkyl adipate, a glycerol ester, a trialkyl ester of citric acid, an acylated trialkyl ester of citric acid, a trialkyl trimellitate, a glycol dibenzoate, a dialkyl terephthalate, a dialkyl phthalate, a dialkanoyl ester of isosorbide, and a dialkyl ester of a 1,2-, 1,3-, or 1,4-cyclohexanedicarboxylic acid.

7. The composition of claim 6, wherein a molar ratio of the mixture to the plasticizer is in a range from 1:15 to 15:1.

8. The composition of claim 7, further comprising:
at least one polymer selected from the group consisting of polyvinyl chloride, polyvinylbutyral, polylactic acid, polyhydroxybutyral, and polyalkyl methacrylate.

9. A composition, comprising:
the mixture of claim 1; and
at least one polymer selected from the group consisting of polyvinyl chloride, polyvinylbutyral, polylactic acid, polyhydroxybutyral, and polyalkyl methacrylate.

10. The composition of claim 9, wherein a ratio of the polymer to the mixture is in a range from 30:1 to 1:2.5.

11. A process for plasticizing a plastic, the process comprising:
contacting the mixture of claim 1 with a plastic.

12. A process for plasticizing a paint, an ink, an adhesive, an adhesive component, a varnish, a plastisol, or a sealant, the process comprising:
contacting the composition of claim 6 with a paint, an ink, an adhesive, an adhesive component, a varnish, a plastisol, or a sealant.

13. A process for dissolving a paint, an ink, an adhesive, an adhesive component, a varnish, a plastisol, or a sealant, the process comprising:
contacting the composition of claim 6 with a paint, an ink, an adhesive, an adhesive component, a varnish, a plastisol, or a sealant.

14. A lubricating oil, comprising:
the composition of claim 6.

15. A metal processing auxiliary, comprising:
the composition of claim 6.

16. The process of claim 3, wherein the isomeric C9 alcohols have an empirical formula of $C_9H_{19}OH$.

17. The process of claim 3, wherein the isomeric C9 alcohols have an empirical formula of $C_8H_{17}CH_2OH$.

18. The process of claim 17, wherein the mixture comprising isomeric C9 alcohols comprises less than 10 mol % of 3,5,5-trimethylhexanol or a trisubstituted nonyl alcohol of empirical formula $C_8H_{17}CH_2OH$.

19. The process of claim 17, wherein the mixture comprising isomeric C9 alcohols comprises less than 5 mol % of 3,5,5-trimethylhexanol or a trisubstituted nonyl alcohol of empirical formula $C_8H_{17}CH_2OH$.

20. The process of claim 17, wherein the mixture comprising isomeric C9 alcohols comprises less than 1 mol % of 3,5,5-trimethylhexanol or a trisubstituted nonyl alcohol of empirical formula $C_8H_{17}CH_2OH$.

* * * * *